United States Patent [19]
Kokura et al.

[11] Patent Number: 5,166,161
[45] Date of Patent: Nov. 24, 1992

[54] 1,3-DICARBONYL COMPOUNDS AND THEIR USE

[75] Inventors: Toshihide Kokura; Kazunari Nakao; Fumitaka Ito; Masami Nakane, all of Groton, Conn.

[73] Assignee: Pfizer Inc., New York, N.Y.

[21] Appl. No.: 644,644

[22] Filed: Jan. 22, 1991

[30] Foreign Application Priority Data

Jan. 22, 1990 [JP] Japan .................................. 2-12342

[51] Int. Cl.$^5$ ................. C07D 417/12; A61K 31/425
[52] U.S. Cl. ...................................... 514/314; 514/337; 514/371; 514/404; 514/432; 514/367; 514/450; 514/456; 514/617; 514/682; 540/593; 546/156; 546/175; 546/269; 546/273; 546/274; 546/309; 548/159; 548/163; 548/195; 548/364.4; 548/372.5; 549/9; 549/60; 549/72; 549/23; 549/355; 549/399; 564/169; 568/327; 568/328

[58] Field of Search ................ 568/327, 328; 564/164; 544/355, 399, 9.60, 72.23; 548/195, 159, 163, 326; 546/156, 175, 269, 273, 274, 309; 540/593; 514/314, 337, 371, 367, 404, 422, 450, 456, 617, 682

[56] References Cited

U.S. PATENT DOCUMENTS 3,591,584  6/1971  Lombardino ...................... 260/243
4,400,543  8/1983  Suarez ................................ 568/327

OTHER PUBLICATIONS

Lombardino, J. G., J. Med. Chem. 16, 493 (1973).
Lombardino, J. G., J. Med. Chem., 11, 342 (1968).
Lombardino, J. G., J. Med. Chem., 13, 206 (1970).
Kadin, S. B., Wiseman, E. H., Nature, 222, 275 (1969).

Primary Examiner—Robert Gerstl
Attorney, Agent, or Firm—Peter C. Richardson; J. Trevor Lumb; Gregg C. Benson

[57] ABSTRACT

3-Oxo-4-acyl or carbamyl-bicyclic aromatic and heterocyclic compounds as inhibitors of cyclooxygenase and lipoxygenase and useful as antiallergy and antiinflammatory agents.

17 Claims, No Drawings

1,3-DICARBONYL COMPOUNDS AND THEIR USE

BACKGROUND OF THE INVENTION

This invention relates to novel 1,3-dicarbonyl compounds and their use. The new compounds of the present invention are inhibitors of both the cyclooxygenase (CO) and lipoxygenase (LO) enzymes, and are of use in the treatment or alleviation of allergic or inflammatory conditions in mammals including humans.

Arachidonic acid is known to be the biological precursor of several groups of endogenous metabolites, prostaglandins including prostacyclins, thromboxanes and leukotrienes. The first step of the arachidonic acid metabolism is the release of esterified arachidonic acid and related unsaturated fatty acids from membrane phospholipids, via the action of phospholopase. Free fatty acids are then metabolized either by cyclooxygenase to produce the prostaglandins and thromboxanes or by lipoxygenase to generate hydroperoxy fatty acids which may be further converted to the leukotrienes. The prostaglandins exhibit diverse physiological effects depending upon their structure. For example, PGE and PGA inhibit gastric secretion as well as lower arterial blood pressure. The thromboxane, especially, thromboxane $A_2$ is a potent vasoconstrictor and platelet aggregatory substance. The leukotrienes are the biological source of the slow reacting substance of anaphylaxis (SRS-A), a chemical mediator in allergic bronchial asthma.

Aspirin and most other non-steroidal antiinflammatory drugs inhibit the cyclooxygenase enzyme. Both antiinflammatory activity and analgesic activity associated with these drugs are rationalized in terms of their inhibition of the action of cyclooxygenase. The lipoxygenase inhibiting activity of one agent, AA861 2,3,5,-trimethyl-6-(12-hydroxy-5,10-cyclodecadiynyl)-1,4benzoquinone, has been reported (see, Yoshimoto et al., Biochem, et Biophys. 713, 470–473(1982). CGS-5391B (C. E. Hock et al., Prostaglandins, 28, 557-571(1984) has recently become known as a combination cycloxygenase and lipoxygenase inhibitor.

PCT Patent Application PCT/JP84/00452 (WO 85/01289) and Japanese patent publication No. 107958/1988 describe and claim a number of benzoxazolone and benzothiazolone derivatives useful for the treatment of inflammatory conditions and thrombosis.

SUMMARY OF THE INVENTION

The compounds of the invention are of the formula

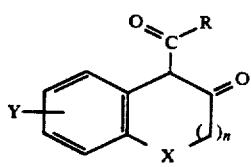

I and the pharmaceutically acceptable salts thereof, wherein R is (a) phenyl substituted by fluoro, chloro or dichloro,
(b) thienyl,
(c) phenylalkyl of seven to nine carbon atoms,
(d) phenylamino substituted by fluoro, chloro, trifluoromethyl, dichloro, difluoro, chlorotrifluoromethyl, or trichloro,
(e) pyridylamino,
(f) pyrazolylamino,
(g) benzothiazol-2-ylamino,
(h) thiazol-2-ylamino of the formula

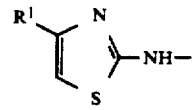

where $R^1$ is hydrogen, alkyl of one to four carbon atoms, phenyl, benzoyl, phenylalkyl of seven to nine carbon atoms, styryl or hydrozyphenyl.

(i) thiazol-2-ylamino of the formula

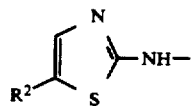

where $R^2$ is chloro, nitro or phenylsulfonyl optionally substituted by chloro, fluoro, methyl, methoxy or nitro, or (j) thiazol-2-ylamino of the formula

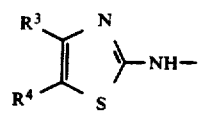

where $R^3$ is phenyl or alkyl of one to four carbon atoms and $R^4$ is phenyl or phenylalkyl of seven to nine carbon atoms; X is $-CH_2-$, $C(CH_3)_2$, O, S or $N-CH_3$; n is an integer of 1 to 2; and Y is hydrogen, methyl, methoxy, fluoro, chloro, trifluoromethyl or quinol-2-ylmethyloxy.

A preferred group of compounds are those where X is $-CH_2-$, O or S, D is 1, Y is hydrogen and R is phenylamino substituted by fluoro, chloro, trifluoromethyl, dichloro, difluoro, chloro-trifluoromethyl or trichloro. Especially preferred within this group are those compounds where X is $-CH_2-$ and R is 3,4-dichlorophenylamino, where X is O and R is 3,4-dichlorophenylamino, where X is S and R is 3,4 dichlorophenylamino, where X is O and R is 4-trifluoromethylphenylamino and where X is O and R is 3-trifluoromethyl-4-chlorophenylamino.

A second group of preferred compounds are those where X is O, n is 1, Y is hydrogen and R is thiazol-2-ylamino of the formula

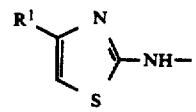

where $R^1$ is hydrogen, alkyl of one to four carbon atoms, phenyl, benzoyl, phenylalkyl of seven to nine carbon atoms, styryl or hydroxyphenyl. Especially preferred within this group are those compounds where $R^1$ is hydrogen, where $R^1$ is phenyl and where $R^1$ is phenyl and where $R^1$ is methyl.

A third group of preferred compounds are those where X is O, n is 1, Y is hydrogen and R is thiazol-2-ylamino of the formula

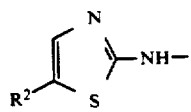

where $R^2$ is chloro, nitro or phenylsulfonyl optionally substituted by chloro, fluoro, methyl, methoxy or nitro. Especially preferred in this group is the compound where $R^2$ is chloro.

A fourth group of preferred compounds are those where D is 1 and Y is hydrogen. Especially preferred within this group is the compound where X is $-CH_2-$ and R is 2-thienyl.

The present invention includes a method for treating an allergic or inflammatory in a human being in need of such treatment which comprises administering to said human being an antiallergic or antiinflammatory effective amount of a compound of formula I.

The present invention also includes a pharmaceutical composition for administering to a human being which comprises a compound of the formula I and a pharmaceutically acceptable carrier or diluent.

The pharmaceutically acceptable salts of the compounds of the formula (I) containing a basic nitrogen are those formed from acids which form non-toxic acid addition salts, for example, the hydrochloride, hydrobromide, sulfate or bisulfate, phosphate, acetate, citrate, fumarate, gluconate, lactate, maleate, succinate, tartrate, methanesulfonate, benzenesulfonate toluenesulfonate and formate salts.

As one skilled in the art will appreciate, the 1,3-dicarbonyl structure of the compounds of the present invention is capable of undergoing enol-keto tautomerism with the two forms in equilibrium:

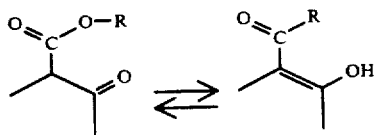

The present application is meant to embrace both forms of this tautomerization.

In addition, this 1,3-dicarbonyl structure is also capable of forming salts with bases. These include such organic bases as triethylamine, ethanolamine and triethanolamine, and such inorganic bases as alkali metal hydroxides or alkaline earth metal hydroxides.

DETAILED DESCRIPTION OF THE INVENTION

The compounds of the present invention can be prepared by several methods. Method A comprises the reaction as shown:

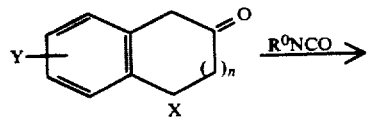

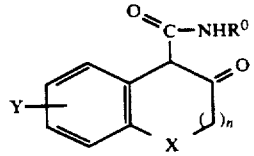

where Y, X and are as indicated and $R^0$ is said substituted phenyl.

The reaction is carried out by adding about an equimolar amount of the appropriate isocyanate to a solution or suspension of equimolar amounts of the requisite ketone and a base, such as sodium hydride or an alkali metal hydroxide or carbonate in a reaction-inert solvent such as tetrahydrofuran, dimethylformamide or dimethylsulfoxide. The preferred reaction temperature is about 0°-80° C. and the reaction time of 2-12 hours.

On completion, the product is isolated by conventional methods and purified by recrystallization or column chromatography.

A second method for preparing compounds of the present invention, Method B, is shown as follows:

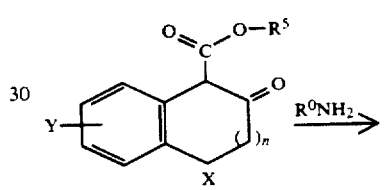

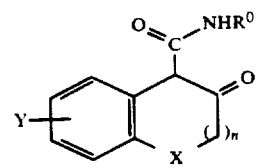

where X, Y and n are as defined, $R^5$ is lower alkyl and $R^0$ is said substituted phenyl, pyridyl, pyrazolyl, benzothiazol-2-yl, said thiazol-2-yl of the formulae

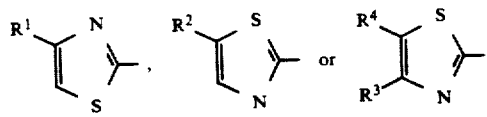

where $R^1$, $R^2$, $R^3$ and $R^4$ are as defined.

The reaction is carried out by heating approximately equimolar amounts of the requisite ester and amine in a reaction-inert solvent such as benzene, toluene or xylene at a reaction temperature of about 75°-130° C. for about 2-5 hours under a nitrogen atmosphere.

The product is isolated by concentration of the solvent to the point of crystallization or all the reaction solvent can be removed and the residual product induced to crystallizing by trituration with an appropriate solvent.

Purification of the product is carried out by conventional means.

A third method for the synthesis of compounds of the present invention, Method C, is as follows:

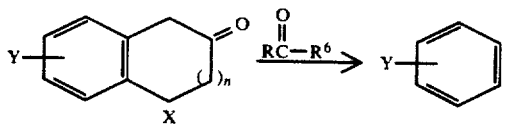

where X, Y and n are as defined, $R^6$ is phenylthio or p-nitrophenoxy and R is phenylalkyl, substituted phenyl or thienyl.

The reaction is carried out by adding a molar amount of an appropriate ester to a solution or suspension of about equimolar amounts of the requsite ketone and a base in a reaction-inert solvent such as tetrahydrofuran, dimethylformamide or dimethylsulfoxide at 0°-50° C. for 4-10 hours.

Bases suitable to form an anion of the ketone include sodium hydride, alkali metal hydroxides or carbonates and lithium diisopropylamide.

Isolation and purification of the product is carried out by conventional means.

The pharmaceutically acceptable salts of the novel compound of formula (I) containing a basic nitrogen are readily prepared by contacting said compound with a stoichiometric amount of an appropriate mineral or organic acid in either an aqueous solution or a suitable organic solvent. The salt may then be obtained by precipitation or by evaporation of the solvent. Among those salts enumerated earlier, an especially preferred salt is the hydrochloride.

As previously indicated, compounds of the present invention also are capable of forming salts with inorganic or organic bases. These salts are readily prepared by containing said compound with a stoichiometric amount of an appropriate inorganic or organic base in either an aqueous solution or a suitable organic solvent. The salt may then be obtained by precipitation or by evaporation of the solvent. Among those salts enumerated earlier, an especially preferred salt is the sodium salt.

The compounds of formula (I) possess inhibiting activity on the action of the cyclooxygenase as well as on the action of the lipoxygenase. This activity has been demonstrated by a cell culture assay using rat peritoneal cavity resident cells which determines the effect of said compounds on the metabolism of arachidonic acid.

The ability of the compounds of formula (I) to inhibit both enzymes make them useful for controlling the symptoms induced by the endogenous metabolites arising form arachidonic acid in a mammalian subject. The compounds are thereof valuable in the prevention and treatment of such disease states in which the accumulation of said arachidonic acid metabolite is the causative factor, e.g., allergic bronchial asthma, skin disorders, rheumatoid arthritis, osteoarthritis, and thrombosis.

Since conventional non-steroidal inflammatory agents such as aspirin only inhibit cyclooxygenase, they suppress inflammatory conditions as well as tend to cause adverse gastrointestinal reaction by virtue of the enzyme inhibition. Compounds of the present invention, however, are gastrointestinally cytoprotective in addition to possessing anti-allergy and anti-inflammatory activities. Thus, they show less adverse effects and are of value for use as a safe drug.

When a compound of the formula (I) or a pharmaceutically acceptable salt thereof is to be used as either an anti-allergic agent or an anti-inflammatory agent, it can be administered to a human subject either alone, or preferably, in combination with pharmaceutically acceptable carriers or diluents in a pharmaceutical composition, in accordance with standard pharmaceutical practice. A compound can be administered by a variety of conventional routes of administration including orally, parenterally and by inhalation. When the compounds are administered orally, the dose range will be form about 0.1 to 20 mg/kg body weight of the be treated per day in single or divided doses. If parenteral administration is desired, then an effective dose will be from 0.1 to 1.0 mg/kg body weight of the subject to be treated per day. In some instance it may be necessary to use dosages outside these limits, since the dosage will necessarily vary according to the age, weight and response of the individual patient as well as the severity of the patient's symptoms and the potency of the particular compound being administered.

For oral administration, the compounds of formula (I) can be administered, for example, in the form of tablets, powders, lozenges, syrups or capsules, or as an aqueous solution or suspension. In the case of tablets for oral use, carriers which are commonly used include lactose and corn starch, and lubrication agents, such as magnesium stearate, are commonly added. In the case of capsules, useful diluents are lactose and dried corn starch. When aqueous suspensions are required for oral use, the active ingredient is combined with emulsifying and suspending agents. If desired, certain sweetening and/or flavoring agents may be added. For intramuscular, intraperitonela, subcutaneous and intravenous use, sterile solutions of the active ingredient are usually prepared, and the pH of the solutions should be suitably adjusted and buffered.

The present invention is illustrated by the following examples. However, it should be understood that the examples are simply illustrative and the invention is not limited to the specific details of these examples. Proton nuclear magnetic resonance spectra (NMR) were measured at 270 MHz unless otherwise indicated for solutions in perdeuterodimethyl sulfoxide (DMSO-$d_6$) and peak positions are expressed in parts per million (ppm) downfield from tetramethylsilane. The peak shapes are denoted as follows: s, singlet; d, doublet; t, tripelt; q, quartet; m, multiplet; b, broad.

EXAMPLE 1

N-3,4-Dichlorophenyl-2-hydroxy-6-methoxy-3,4-dihydronaphthalene-1-carboxamide

A solution of 6-methoxy-2-tetralone (1.0 g, 5.68 mmol) in dry tetrahydrofuran (5 ml) was added to a suspension of sodium hydride (251 mg, 6 27 mmole) in dry tetrahydrofuran (5 ml) at 0°-5° C. under nitrogen. To this reaction mixture a solution of 3,4-dichlorophenyl isocyanate (1.17 g, 6.24 mmole) was added at room temperature and the reaction was heated at reflux for 2 hr. After cooling, the reaction mixture was acidified with 1N hydrochloric acid and extracted with ether (30 ml × 3). The combined organic layers were dried over magnesium sulfate. Filtration and evaporation of the solvents afforded solids, which were purified by silica gel chromatography (BW300, n-Hexane/EtOAc = 10/1). The desired fractions were collected and recrystallized from n-Hexane ethyl acetate to afford 0.57 q (1.57 mmole, 28%) of the desired product.

mp: 120.5°-121.5° C.

IR (KBr cm$^{-1}$): 3360,1630,1600,1580,1530

1H NMR (270 MHz, CDCl₃, TMS δ): 13.62 (1H, s), 7.76 (1H, d, J=2.4Hz), 7.70 (1H, br.s), 7.40 (1H, d, J=8.8 Hz), 7.33 (1H, dd, J=8.8, 2.4Hz), 7.26 (1H, d, J=8.8Hz), 6.83-6.79 (2H, m), 3.83 (3H, s), 2.81 (2H, m), 2.49 (2H ,m).

Elemental Analysis: Calcd. for $C_{18}H_{15}NO_3Cl_2$; C; 59.36%, H;4.15%, N; 3.85%; Found: C;59.25% H;4.19%, N;3.77%.

Similarly the following compounds were prepared. Example 2-11

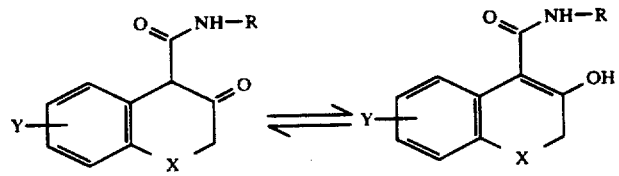

| example NO | R | X | Y | m.p.(°C.) | IR (KBr, cm⁻¹) | ¹HNMR (δ:) |
|---|---|---|---|---|---|---|
| 2 | phenyl | CH₂ | H | 102-103 | 3650-3200, 1710 1640, 1600 | 7.91(1H, br.s), 7.41-7.08(9H, m), 4.51(1H, s), 3.35-3.23(1H, m), 3.05-2.81(2H, m), 2.48-2.63(1H, m) (CDCl₃) |
| 3 | 4-Cl-phenyl | CH₂ | H | 107-108 | 3650-3200, 3300 1720, 1650, 1600 1540 | 13.95(0.62H, s), 8.00(0.38H, br.s), 7.75(0.62H, br.s), 7.49-7.13(8H, m), 4.50(0.38H, s), 3.33-2.47(4H, m) (CDCl₃) |
| 4 | 3,4-diCl-phenyl | CH₂ | H | 101.7-102.5 | 3300, 3200, 1720 1660, 1530 | 8.12(1H, br.s), 7.77(1H, d,J=2.2Hz), 7.37-7.19(6H, m), 4.51(1H, s), 3.50-3.19(1H, m), 3.06-2.96(1H, m), 2.90-2.80(1H, m) (CDCl₃) |
| 5 | 3,4-diCl-phenyl | CH₂ | 6-Cl | 171.0-171.6 | 3420, 1625, 1580 1505 | 13.79(0.87H, s)8.19(0.13H, br.s), 7.77(0.13H, d, J=2.2Hz)7.75(0.87H, d, J=2.2Hz), 7.59(0.87H, br.s), 7.40(0.87H, d, J=8.4Hz), 7.38-7.10 (4.13H, m), 4.48(0.13H, s), 3.22-2.87 (0.26H, m), 2.84-2.78(1.74H, m), 2.63-2.47(1.87H, m) (CDCl₃) |
| 6 | 3,4-diCl-phenyl | CH₂ | 6-CH₃ | 145.5-147.1 | 3250, 1710, 1660 1580, 1520 | 13.75(0.64H, s)8.08(0.64H, br.s), 7.76(1.36H, m)7.41-7.06(5H, m), 4.47(0.36H, s), 3.25-3.14(0.36H, m), 3.00-2.78(2H, m), 2.62-2.48(1.64H, m), 2.37(1.08h, s), 2.34(1.92H, s) (CDCl₃) |
| 7 | 3,4-diCl-phenyl | C(CH₃)₂ | 6-OCH₃ | 131.2-132.3 | 3400, 2950, 1610 1570, 1500 | 13.49(0.86H, s), 8.46(0.14H, br.s), 7.38(0.14H, d, J=1.5Hz), 7.77(0.86H, d, J=1.5Hz), 7.42-7.26(3H, m), 7.11(0.14H, d, J=8.8Hz)7.01(0.14H, d, J=2.6Hz), 6.95(0.86H, d, J=2.6Hz), 6.98(0.14H, dd, J=8.8, 2.6Hz), 6.79(0.86H, dd, J=8.8, 2.6Hz), 4.49(0.14H, s), 3.85(0.42H, s), 3.84(2.58H, s), 2.38(2H, s), 1.32(6H, s) (CDCl₃) |
| 8 | 3,4-diCl-phenyl | O | H | 139.7-141.4 | 3430, 3280, 1630 1580, 1520 | 13.31(1H, s)7.77(1H, d, J=2.4Hz) 7.69(1H, br.s)7.41(1H, d, J=8.8Hz) 7.36-7.03(6H, m)4.60(2H, s) (CDCl₃) |
| 9 | 3,4-diCl-phenyl | O | 6-Cl | 139-140 | 3430, 1630, 1580 1520, 1480 | 13.41(1H, br.s), 7.78(1H, d, J=2.4Hz), 7.56(1H, br.s), 7.43(1H, d, J=8.8Hz), 7.31(1H, dd, J=8.8, 2.5Hz), 7.30(1H, d, J=2.5Hz), 7.10(1H, dd, J=8.3, 2.4Hz), 6.97(1H, d, J=8.8Hz), 4.60(2H, s) (CDCl₃) |

-continued

Similarly the following compounds were prepared. Example 2–11

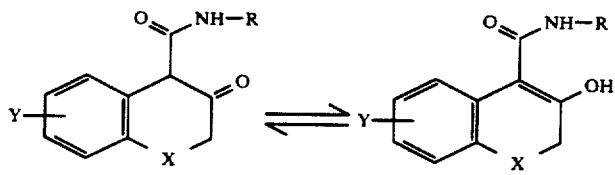

| example NO | R | X | Y | m.p.(°C.) | IR (KBr, cm$^{-1}$) | $^1$HNMR (δ:) |
|---|---|---|---|---|---|---|
| 10 | 3,4-dichlorophenyl | S | H | 110–111 | 3430, 1630, 1580 1520 1480 | 14.14(1H, br.s), 7.64–7.05(8H, m) 3.31(2H, s) (CDCl$_3$) |

EXAMPLE 11

N-2-(4-phenyl)thiazolyl-3-hydroxy-2H-chromene-4-carboxamide

A mixture of ethyl 3-hydroxy-2H-chromene-4-carboxylate (1.0 g, 4.5 mmole) and 2-amino-4-phenylthiazole (4.1 g, 23 mmol) in dry toluene (100ml) was heated at reflux for 3 hr under nitrogen. After cooling the reaction mixture, the solvent was removed under reduced pressure. Methanol was added into the resulting residue, which was stirred for 3 hr at room temperature. The resulting precipitate was collected and dried in vacuo for 8 hr to afford the product (1.3 g, 3.6 mmole, 81%)

mp: 215°–216° C.

IR (KBr, cm 3700–3200,1640,1600,1570,1530

$^1$H NMR (270 MHz, DMSO-d$_6$, δ): 13.40 (1H, br.s), 7.90–7.82 (3H, m), 7.59 (1H, s), 7.49–7.33 (3H, m), 7.01–6.81 (3H, m), 4.67 (2H, s).

Elemental Analysis: Calcd. for C$_{19}$H$_{14}$N$_2$O$_3$S: C;65.13%, H;4.03%, N;8.60%. Found; C;64.71%, H;4.10%, N;7.95%

Similarly the following compounds were prepared. Example 12-37

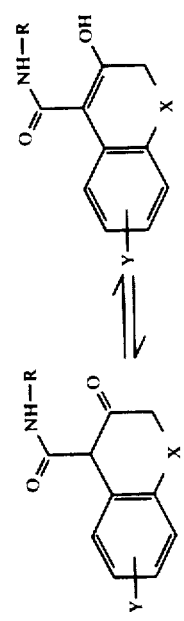

| example NO | R | X | Y | m.p. (°C.) | IR (KBr, cm$^{-1}$) | $^1$H NMR (δ:) |
|---|---|---|---|---|---|---|
| 12 | (thiazole) | O | H | 192.5-192.8 (dec.) | 3120, 3050, 1670 1570, 1500 | 15.46(1H, br.s), 8.19(1H, d, J=6.4Hz)7.56(1H, d, J=4.4Hz), 7.17(1H, d, J=4.4Hz) 6.96-6.78(4H, m), 4.57(2H, s) (DMSO-d$_6$) |
| 13 | (benzothiazole) | O | H | 210.2-210.7 (dec.) | 1660, 1490, 1405 1280 | 14.99(1H, br.s)8.18(1H, br.d, J=6.8Hz)7.96(1H, d, J=7.8Hz), 7.84-7.29H, m), 7.00-6.81(3H, m), 4.63(2H, s) (DMSO-d$_6$) |
| 14 | (4-CH$_3$, 2-thiazole) | O | H | 250-260 (dec.) | 3650-3200, 1640 1620, 1540, 1490 | 8.25(1H, br.s), 6.76-6.93(3H, m), 6.73(1H, d, J=1.1Hz)4.53(2H, s) 2.27(3H, d, J=1.1Hz) (DMSO-d$_6$) |
| 15 | (4-Cl, 2-thiazole) | O | H | 190 (dec.) | 1640, 1600, 1520, 1490, 1280 | 13.32(1H, br.s), 7.80(1H, d, J=6.8Hz)7.59(1H, s), 6.80-7.24(4H, m) 4.65(2H, s) |
| 16 | (4-NO$_2$, 2-thiazole) | O | H | 195-197 (dec.) | 3650-3300, 1640 1600, 1540, 1490 | 14.30(1H, br.s), 8.61(1H, s), 8.00-7.58(2H, m), 6.94-6.77(3H, m), 4.52(2H, s) (DMSO-d$_6$) |
| 17 | (4-(4-NO$_2$-phenylsulfonyl), 2-thiazole) | O | H | 244-245 (dec.) | 3700-3100, 1660 1600, 1530, 1490 | 13.80(br.s), 8.44-7.80(7H, m), 6.92-6.77(3H, m), 4.54(2H, s) (DMSO-d$_6$) |

-continued

| No. | Structure | mp | IR | NMR |
|---|---|---|---|---|
| 18 | 4-HO-C6H4-thiazole (O,H substituents; 2-methyl thiazole with 4-hydroxyphenyl) | 226–228 (dec.) | 3350, 1640, 1550 1500 | 14.40–13.65(1H, br.s), 10.10–9.50(1H, br.s), 7.97(1H, s), 7.68(2H, d, J=8.8Hz), 7.29(1H, s), 6.96–6.80(5H, m), 4.62(2H, s) (DMSO-$d_6$) |
| 19 | benzyl-thiazole with CH3 | 216.9–217.6 (dec.) | 3425, 3030, 2495 1645, 1599, 1539 | 16.1(1H, br.s)8.23(1H, br.d, J=5.4Hz), 7.37–7.22(6H, m)6.92–6.76(3H, m), 4.53(2H, s)4.00(2H, s), 2.28(3H, s) (DMSO-$d_6$) |
| 20 | phenethyl-thiazole | 211.6–213.4 (dec.) | 3020, 2982, 1645 1612, 1601, 1530 | 15.8(1H, br.s), 8.23(1H, br.d, J=6.4Hz), 7.33–7.17(6H, m)4.56(2H, s), 2.93(4H, m) (DMSO-$d_6$) |
| 21 | styryl-thiazole | 169.3–169.7 (dec.) | 1645, 1599, 1569 1481 | 14.26(1H, br.s), 8.00(1H, br.s), 7.57(2H, d, J=6.3Hz), 7.43–7.14(7H, m), 6.98–6.8(3H, m), 4.62(2H, s) (DMSO-$d_6$) |
| 22 | diphenyl-thiazole | 206.6–208.8 (dec.) | 3400, 3135, 1641 1598, 1568, 1529 | 14.0(1H, br.s), 7.95(1H, br.s)7.46–7.31(11H, m)6.99–6.81(3H, m)4.64(2H, s) (DMSO-$d_6$) |
| 23 | tBu-thiazole (2-methyl, 4-tBu) | 196–198 (dec.) | 3700–3300, 1630 1590, 1530 | 8.19(1H, br.s), 6.92–6.77(3H, m)6.72(1H, s), 4.56(2H, s), 1.29(9H, s) (dmso-$d_6$) |

-continued

| # | Structure | | | |
|---|---|---|---|---|
| 24 | [2-methylthiazol-4-yl phenyl ketone] | O H | 175–176 (dec.) | 3700–3300, 1640 1520 1485, 1440 | 13.08(1H, br.s), 8.03–8.00(3H, m)7.76–7.65(2H, m), 7.56(2H, t, J = 7.8Hz) 7.02–6.82(3H, m), 4.69(2H, s) (DMSO-d₆) |
| 25 | [2-methylpyridine] | O H | 197.6–198.9 (dec.) | 3070, 1650, 1570 1490, 1435 | 8.27–8.11(3H, m), 7.62(1H, br.s)7.26–7.24(1H, m), 6.87–6.76(4H, m) 4.40(2H, s) (DMSO-d₆) |
| 26 | [3-methylpyrazole NH] | O H | 253–256 (dec.) | 3300, 1670, 1600 1520, 1380 | 11.11(1H, s), 7.41(1H, s), 7.38(1H, d, J = 2Hz)7.32(1Hbr.d, J = 8Hz), 7.16(1H, br.dd, J = 7.7, Hz), 6.92(1H, br.dd, J = 8.8Hz), 6.79(1H, br.d, 7Hz), 5.53(1H, d, J = 2Hz), 4.96(1H, d, J = 11.2Hz), 4.07(1H, s), 4.04(1H, d, J = 11.2Hz) (DMSO-d₆) |
| 27 | [2,4-difluorophenyl] | O H | 150–151 | 3350, 1650, 1620 1550, 1520, 1500 | 10.74(0.17H, s), 10.30(0.83H, s)7.93–7.70(1H, m), 7.43–6.81(6H, m) 4.73(0.17H, s), 4.70(1.66H, s)4.61(0.34H, s) (DMSO-d₆) |
| 28 | [2,5-difluorophenyl] | O H | 108–109 | 3420, 1640, 1610 1540, 1490 | 10.31(0.19H, s), 9.92(0.81H, s), 7.94–7.31(3H, m), 7.12–6.85(4H, m), 4.93(0.18H, s), 4.68(1.62H, s), 4.60(0.38H, s) DMSO-d₆ |
| 29 | [2,3-dichlorophenyl] | O H | 154–156 | 3700–3200, 3400 1640, 1580, 1520 | 13.35(1H, s), 8.42–8.38(2H, m), 7.52–7.48 (1H, m), 7.43(1H, d, J = 9.3Hz), 7.21–7.03(3H, m), 4.62(2H, s) (CDCl₃) |
| 30 | [4-trifluoromethylphenyl] | O H | 124–125 | 3700–3200, 3420 1640, 1610, 1530 | 13.34(1H, s), 7.83(1H, br.s), 7.68–7.60(4H, m), 7.37(1H, dd, J = 7.3, 2.0Hz), 7.21–7.04(3H, m), 4.61(2H, s) (CDCl₃) |

-continued

| | | | m.p. (°C.) | IR(KBr, cm⁻¹) | ¹H NMR (δ) |
|---|---|---|---|---|---|
| 31 | ![Cl-CF3 phenyl] | O H | 133–135 | 3380, 1650, 1620, 1590, 1540, 1500 | 13.25(1H, s), 7.87–7.69(3H, m), 7.50(1H, d, J=8.8Hz), 7.35(1H, dd, J=7.3, 1.5Hz) 7.21–7.03(3H, m), 4.61(2H, s) (CDCl₃) |
| 32 | ![Cl-Cl phenyl] | O H | 173–174 | 3700–3200, 3400 1650, 1620, 1570 | 13.32(1H, s), 8.71(1H, s), 8.37(1H, br.s), 7.51–7.44(2H, m), 7.21–7.03(3H, m), 4.62(2H, s) (CDCl₃) |
| 33 | ![thiazole] | CH₂ H | 157.5–158.3 (dec.) | 3270, 2950, 1640 1280 | 13.26(0.92H, br.s), 9.70(1H, br.s), 7.42–7.10(5H, m), 6.99(0.92H, d, J=3.7Hz), 6.87(0.08H, d, J=3.7Hz), 4.61(0.08H, s), 3.42–3.29(0.2H, m), 3.10–2.82(2H, m), 2.68–2.51(1.92H, m) (CDCl₃) |
| 34 | ![phenyl-thiazole] | O 6-OCH₃ | 174.3–175.0 (dec.) | 3410, 2900, 2865 1642, 1611, 1594 1531 | 13.73(1H, br.s)7.88(2H, d, J=7.3Hz), 7.56(1H, br.s), 7.49–7.36(5H, m), 6.74(1H, d, J=8.8Hz), 6.55(1H, m), 4.56(2H, br.s), 3.69(3H, s) (DMSO-d₆) |
| 35 | ![quinoline-thiazole] | O 6-(2-quino-lynomethyloxy) | 201.3–202.9 (dec.) | 3720–3340, 1645 1486, 1424, 1192 | 15.64(1H, br.s), 8.46(1H, d, J=8.8Hz), 8.07–8.00(3H, m), 7.84–7.56(4H, m), 7.17(1H, d, J=4.4Hz), 6.72(1H, d, J=8.8Hz), 6.60(1H, dd, J=8.8, 2.9Hz), 5.31(2H, s), 4.63(2H, s) (DMSO-d₆) |

| example NO | structure | m.p. (°C.) | IR(KBr, cm⁻¹) | ¹H NMR (δ) |
|---|---|---|---|---|
| 36 | ![complex structure with Cl, CF3, OH, O, NH] | 133.5–134.3 | 3365, 1631, 1611 1587, 1539, 1497 | 14.5(1H, s), 7.76(1H, J=2.4Hz)7.64(1H, dd<J=8.3Hz), 7.74–7.20(6H, m) 4.63(2H, br.m), 2.49(2H, br.m) (CDCl₃) |

| | | -continued | |
|---|---|---|---|
| 37 | 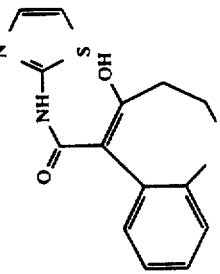 | 184.6–186.4 (dec.) | 3200, 1630, 1605 1535, 1487 | 13.68(1H, br.s), 9.08(1H, br.s)7.37–7.15(5H, m), 6.97(1H, d, J=3.4Hz) 4.61(2H, br.m), 2.48(2H, br.m). (CDCl₃) |

EXAMPLE 38

1-(2-Thenoyl)-2-hydroxy-3,4-dihydronaphthalene

A solution of β-tetralone 1.0 g, 6.8 mmole) in dry tetrahydrofuran (5 ml) was added to a suspension of sodium hydride (278 mg, 7.5 mmole) in dry tetrahydrofuran (10 ml) at 0°-5° C. and the reaction was stirred at room temperature for 10 min. A solution of S-phenyl-2-thiophenethioate (1.66 g, 7.5 mmol) in dry tetrahydrofuran (5 ml) was added to the reaction, which was stirred at room temperature for 5 hr. Water was added to the reaction mixture and the product was extracted with ethyl acetate twice. The combined organic layers were washed with brine and dried over magnesium sulfate. After filtration and evaporation of the solvent, a crude oil was obtained, which was purified by silica gel chromatography (BW300, n-Hexane/ethyl acetate 10/1) to give 1.2g (4.7 mmole, 62%) of the titled product.

IR (KBr, cm$^{-1}$): 3120,3050,1720,1655,1580

$^1$H NMR (270 MHz-CDCl$_3$-TMS δ): 15.75 (0.75H, br.s), 7.97 (0.25H, dd, J=3.9,1.0 Hz), 7.72 (0.75H, dd, J=4.9, 1.0 Hz), 7.64-6.93 (5H, m), 5.33 (0.25H, s), 3.85-3.46 (0.25H, m), 3.06-2.85 (2H, m), 2.64-2.52 (1.5H, m)

Elemental Analysis: Calcd. for C$_{15}$H$_{12}$O$_2$S: C;70.29%, H;4.72%: Found C;70.23%, H;4.68%:

(d) phenylamino substituted by fluoro, chloro, trifluoromethyl, dichloro, difluoro, chlorotrifluoromethyl or trichloro,
(e) pyridylamino,
(f) pyrazolylamino,
(g) benzothiazol-2-ylamino,
(h) thiazol-2-ylamino of the formula

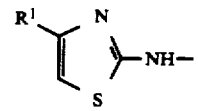

wherein R$^1$ is hydrogen, alkyl having one to four carbon atoms, phenyl, benzoyl, phenylalkyl having seven to nine carbon atoms, styryl or hydroxyphenyl, (i) thiazol-2-ylamino of the formula

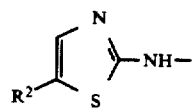

wherein R$^2$ is chloro, nitro or phenylsulfonyl op-

| example NO | structure | m.p. (°C.) | IR(cm$^{-1}$) | $^1$H NMR (δ:) |
|---|---|---|---|---|
| 39 | 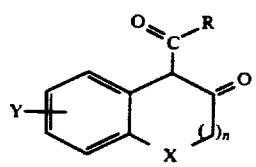 | 123-124 | 3600-3200, 1590 1540, 1460 (KBr) | 16.19(1H, s), 7.67(1H, d, J=2Hz) 7.36(1H, d, J=8Hz), 7.27(1H, dd, J=8.2Hz) 7.05(1H, dt, J=7.3Hz), 6.90(1H, dt, J=7.8, 1.5Hz 6.65(1H, dJ=7.8Hz), 2.97(2H, t, J=7.3Hz) 2.66-2.61(2H, m) (CDCl$_3$) |
| 40 | 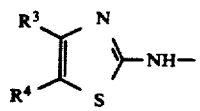 | 59.3-60.3 | 2935, 1747, 1664 1601, 1494 (neat) | 7.35-6.97(9H, m), 6.16(1H, s) 3.05-2.98(4H, m), 2.80-2.75(2H, m) 2.48-2.42(2H, m) (CDCl$_3$) |

We claim:
1. A compound of the formula and the pharmaceutically acceptable salts, thereof, wherein R is
(a) phenyl substituted by fluoro, chloro or dichloro,
(b) thienyl,
(c) phenylalkyl having from seven to nine carbon atoms, tionally substituted by chloro, fluoro, methyl, methoxy or nitro, or
(j) thiazol-2-ylamino of the formula wherein R$^3$ is phenyl or alkyl having one to four carbon atoms and R$^4$ is phenyl or phenylalkyl having seven to nine carbon atoms;
X is —CH$_2$—, C(CH$_3$)$_3$, O, S, or NCH$_3$; n is an integer of 1 to 2; Y is hydrogen, methyl, methoxy, fluoro, chloro, trifluoromethyl or quinol-2-ylmethyloxy.

2. A compound of claim 1, wherein X is —CH$_2$—, O or S; n is 1, Y is hydrogen and R is phenylamino substituted by fluoro, chloro trifluoromethyl, dichloro, difluoro, chloro-trifluoromethly or trichloro.

3. The compound of claim 2, wherein X is —CH$_2$— and R is 3,4-dichlorophenylamino.

4. The compound of claim 2, wherein X is O and R is 3,4-dichlorophenylamino.

5. The compound of claim 2, wherein X is S and R is 3,4-dichlorophenylamino.

6. The compound of claim 2, wherein X is O and R is 4-trifluoromethylphenylamino.

7. The compound of claim 2, wherein X is O and R is 3-trifluoromethyl-4-chlorophenylamino.

8. A compound of claim 1, wherein X is O, n is 1, Y is hydrogen and R is thiazol-2-ylamino of the formula

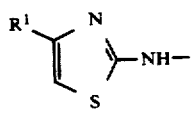

wherein R$^1$ is hydrogen, alkyl having one to four carbon atoms, phenyl, benzoyl, phenylalkyl having seven to nine carbon atoms, styryl or hydroxyphenyl.

9. The compound of claim 8, wherein R$^1$ is hydrogen.

10. The compound of claim 8, wherein R$^1$ is phenyl.

11. The compound of claim 8, wherein R$^1$ is methyl.

12. A compound of claim 1, wherein X is O, n is 1, Y is hydrogen and R is thiazol-2-ylamino of the formula

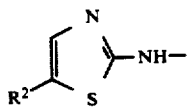

where in R$^2$ is chloro, nitro or phenylsulfonyl optionally substituted by chloro, fluoro, methyl, methoxy or nitro.

13. The compound of claim 12, wherein R$^2$ is chloro.

14. A compound of claim 1, therein n is 1 and Y is hydrogen.

15. The compound of claim 14, wherein X is —CH$_2$— and R is 2-thienyl.

16. A method for treating an allergic or inflammatory condition in a human being in need of such treatment which comprises administering to said human being an antiallergic or antiinflammatory effective amount of a compound according to claim 1.

17. A pharmaceutical composition for administration to a human being which comprises a compound according to claim 1 and a pharmaceutically acceptable carrier or diluent.

* * * * *